(12) United States Patent
Sutton et al.

(10) Patent No.: US 11,980,730 B2
(45) Date of Patent: May 14, 2024

(54) ANCHORED DILATOR SYSTEM AND METHODS FOR SAME

(71) Applicant: Surmodics, Inc., Eden Prairie, MN (US)

(72) Inventors: Gregg Sutton, Eden Prairie, MN (US); Charles Olson, Eden Prairie, MN (US); Karl V. Ganske, Hopkins, MN (US)

(73) Assignee: Surmodics, Inc., Eden Prairie, MN (US)

( * ) Notice: Subject to any disclaimer, the term of this patent is extended or adjusted under 35 U.S.C. 154(b) by 414 days.

(21) Appl. No.: 17/123,512

(22) Filed: Dec. 16, 2020

(65) Prior Publication Data
US 2021/0178134 A1 Jun. 17, 2021

Related U.S. Application Data

(60) Provisional application No. 62/949,024, filed on Dec. 17, 2019.

(51) Int. Cl.
*A61M 29/02* (2006.01)

(52) U.S. Cl.
CPC ....... *A61M 29/02* (2013.01); *A61M 2029/025* (2013.01); *A61M 2210/12* (2013.01)

(58) Field of Classification Search
CPC ...... A61M 16/0484; A61M 2025/0687; A61M 2029/025; A61M 2210/12; A61M 25/0074; A61M 25/0662; A61M 29/02
See application file for complete search history.

(56) References Cited

U.S. PATENT DOCUMENTS

| 5,108,413 A | 4/1992 | Moyers |
| 5,824,002 A | 10/1998 | Gentelia et al. |

(Continued)

FOREIGN PATENT DOCUMENTS

| EP | 2446915 A1 | 5/2012 |
| WO | WO-2021126934 A1 | 6/2021 |

OTHER PUBLICATIONS

Gilchrist, Ian C., "Sheathless Guide Catheters During Transradial PCI", vol. 10, No. 5 Cardiac Interventions Today, (Sep. Oct. 2016), pp. 41-44.

(Continued)

*Primary Examiner* — Mohamed G Gabr
(74) *Attorney, Agent, or Firm* — Schwegman Lundberg & Woessner, P.A.

(57) ABSTRACT

An anchored dilator includes a push tube having proximal and distal push tube portions. A dilator tip is coupled with the distal push tube portion and is configured for selectable coupling with a catheter. The dilator tip includes an anchor cuff having a cuff interface. The anchor cuff is configured to transition between a shuttle configuration having a shuttle profile and an anchored configuration having an anchored profile larger than the shuttle profile. A cuff operator assembly is configured to transition the anchor cuff between the anchored and shuttle configurations. The cuff operator assembly includes a cuff operator movably coupled with the dilator tip, and an operator shaft coupled with the cuff operator. The operator shaft extends toward the proximal push tube portion. Actuation of the cuff operator with the operator shaft transitions the anchor cuff between the shuttle configuration and the anchored configuration.

30 Claims, 6 Drawing Sheets

(56) References Cited

U.S. PATENT DOCUMENTS

| | | |
|---|---|---|
| 6,790,221 B2 | 9/2004 | Monroe et al. |
| 7,144,386 B2 | 12/2006 | Korkor et al. |
| 9,114,227 B2 | 8/2015 | Blanchard |
| 9,357,986 B2 | 6/2016 | Stammberger et al. |
| 2001/0053922 A1 | 12/2001 | Zhu et al. |
| 2004/0030319 A1 | 2/2004 | Korkor et al. |
| 2009/0018529 A1 | 1/2009 | Bailey et al. |
| 2011/0028904 A1* | 2/2011 | Watanabe ......... A61M 25/0043 604/164.01 |
| 2015/0297250 A1 | 10/2015 | Farhat et al. |

OTHER PUBLICATIONS

Silva, Michael B., "Guidewires, Catheters, and Sheaths", Endovascular Surgery, Elsevier Inc., (Dec. 1, 2011), pp. 59-69.

"International Application Serial No. PCT/US2020/065252, International Preliminary Report on Patentability dated Nov. 16, 2021", 8 pgs.

"International Application Serial No. PCT/US2020/065252, International Search Report dated Mar. 16, 2021", 3 pgs.

"International Application Serial No. PCT/US2020/065252, Written Opinion dated Mar 16, 2021", 5 pgs.

"European Application Serial No. 20903418.0, Extended European Search Report dated May 19, 2023", 9 pgs.

"European Application Serial No. 20903418.0, Response filed Dec. 14, 2023 to Extended European Search Report dated May 19, 2023", 9 pgs.

\* cited by examiner

ANCHORED DILATOR SYSTEM AND METHODS FOR SAME

PRIORITY APPLICATIONS

This application claims the benefit of priority to U.S. Provisional Patent Application Ser. No. 62/949,024, filed Dec. 17, 2019, the content of which is incorporated herein by reference in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Surmodics, Inc. of Eden Prairie, Minnesota. All Rights Reserved.

TECHNICAL FIELD

This document pertains generally, but not by way of limitation, to medical devices for vascular access and navigation.

BACKGROUND

Catheters and other vascular accessing medical devices are introduced to vasculature and delivered to target locations within the vasculature with a variety of instruments. In one example, a catheter is delivered to a specified location in the vasculature with a collection of instruments including a needle, guidewire, dilator, introducer, guide catheter, catheter based instruments or the like.

The Seldinger technique is one example of a method that uses these instruments to introduce a catheter to the vasculature. A vessel is first penetrated through the skin with a needle. A guidewire is passed into the vessel through a lumen of the needle. The needle is withdrawn, leaving the guidewire in place. A dilator is fed over the guidewire, and an introducer sheath is fed over the dilator. The dilator and the introducer sheath are pushed along the guidewire and into the vessel. The dilator extends from the tip of the introducer sheath, and provides a transition from the guidewire diameter to the inner diameter of the introducer sheath. The dilator is removed leaving the introducer sheath and the guidewire in the vessel and extending from the penetration through the skin. A catheter is fed through the introducer sheath and over the guidewire to the specified location in the vasculature.

In other examples, after penetration and introduction of an introducer sheath, the vasculature is dilated with one or more dilators delivered along the guidewire to the specified target location. After dilation, the guide sheath is navigated through the dilated vasculature to the specified target location. The guide sheath includes a delivery lumen having an inner diameter that permits delivery of a therapeutic catheter, diagnostic catheter or other medical device (having an outer diameter smaller than the inner diameter of the guide sheath) to the specified target.

OVERVIEW

The present inventors have recognized, among other things, that a problem to be solved can include minimizing the devices and steps used for vascular access and delivery, and increasing the profile (e.g., diameter) available for medical devices delivered through the vasculature. The Seldinger technique for vascular introduction and similar techniques for navigation to specified vascular locations are example methods for accessing a specified vascular location. Multiple instruments are used in successive steps to provide access to a vessel and improve access through vasculature to a vascular location. For example, during introduction a needle penetrates the skin and vessel; a guidewire is delivered through the needle to the specified vascular location; the needle is withdrawn; one or more dilators dilate the penetration; and an introducer sheath is delivered over the guidewire (optionally with an intermediate catheter between the guidewire and the sheath inner diameter) to introduce the sheath through the penetration.

The intermediate catheter or dilator is removed, and a guide sheath or guide catheter is delivered over the guidewire, through the introducer sheath, and navigated to the specified vascular location. In a similar manner to the introducer sheath for introduction, in delivery one or more dilators are navigated along the guidewire to the specified vascular location to dilate the vessel. The dilator has a profile proximate to the outer diameter of the guide catheter or guide sheath. The dilator is removed, and the guide catheter (or sheath) is delivered along the guidewire and navigated through the dilated vessels to the specified vascular location. The guide catheter (or sheath) includes its own associated delivery lumen. One or more of therapeutic catheters, diagnostic catheters or other medical devices (collectively medical device), having a device profile smaller than the inner diameter of the guide catheter or sheath, are delivered through the delivery lumen to the specified vascular location. Accordingly, the guide catheter or guide sheath fills a portion of the vessel profile (e.g., based on its wall thickness) and the device profile of the medical device is thereby smaller than a corresponding guide profile of the guide catheter or guide sheath.

Each of these steps and the corresponding instruments are introduced in a staged method to achieve vascular introduction and delivery to the specified vascular location. The number of steps, instruments and staged introduction and removal of instruments are labor and time intensive. Additionally, the introduction of multiple instruments provides multiple vectors for infection. Further still, the delivery and placement of an introducer sheath and one or more of a guide catheter or guide sheath consumes space in the vessel otherwise available for medical devices. In some examples, for instance, with a transradial access (through the wrist) introducer sheath, guide catheter or sheath, or both fill a relatively large portion of the vessel diameter, and accordingly limit the profile of catheters and instruments (herein medical devices) delivered to the specified vascular location.

Further, introducer sheaths, guide catheters or guide sheaths or the like have corresponding profiles larger than the guidewire to facilitate the eventual passage and delivery of medical devices through delivery lumens. Introduction and delivery of the introducer sheath, guide catheter or guide sheath in a procedure over the narrower guidewire provides a steep transition that exposes the edge of the sheath or catheter. In some examples, the exposed edges engage with vessel walls (especially at bends) and increase the risk of trauma to the vessel, an effect sometimes referred to as 'razoring'. An intermediate catheter is optionally provided between the guidewire and the guide catheter or guide sheath to provide a stepped interface. In at least some examples, the stepped interface continues to provide a relatively sharp edge at the end of the guide catheter or guide sheath having the increased risk of trauma.

The present subject matter helps provide a solution to these problems, such as with an anchored dilator system that marries the dilator with medical devices, such as a guide catheter, guide sheath or medical device (e.g., therapeutic or diagnostic catheter) for delivery to the specified vascular location. The intervening introducer sheath, guide catheter or guide sheath used in other methods is thereby optionally eliminated. The dilator of the system includes a dilator tip having an anchor cuff that transitions between a shuttle configuration and an anchored configuration. In the shuttle configuration, the anchor cuff is (relatively) compact, and the distal tip readily passes through the catheter lumen of the guide catheter. A distal nose of the distal tip is delivered through the catheter lumen and projects from the distal catheter portion. The anchor cuff, proximal to the distal nose, is received and remains within the catheter lumen. The anchor cuff is transitioned (e.g., expanded or deployed) to the anchored configuration. The anchored profile of the anchor cuff is larger than in the shuttle configuration, and engages with the catheter, for instance with an interior surface surrounding the catheter lumen. The distal tip of the anchored dilator is thereby anchored to the medical device in the anchored configuration. Optionally, a dilator transition of the dilator tip is deployed with operation of the anchor cuff. The dilator transition provides a flush (including near flush) transition between the tapered dilator nose and the catheter exterior surface of the medical device that conceals (at least partially) the otherwise exposed edge of the medical device, such as the guide catheter. Accordingly, snagging, trauma to the vessel or the like are minimized. Instead, the anchored dilator and the catheter (collectively medical devices) are a composite assembly having a consistent graduated profile.

The anchored dilator system of the medical device, such as a guide catheter, guide sheath, introducer sheath or medical device and the distal tip anchored to the guide catheter are delivered together. For example, manipulation of a push tube of the dilator navigates the dilator tip and the medical device anchored to the dilator tip through the vasculature (e.g., over a guidewire) to the specified vascular location.

By consolidating the dilator and the medical device (including a guide catheter, guide sheath, introducer sheath, therapeutic catheter, or other instrument) together with the anchor cuff both components are navigated to the specified vascular location at the same time. Additionally, time consuming and labor intensive steps, such as delivery of dilators, an introducer sheath, delivery of a guide catheter or guide sheath, and delivery of a catheter over a guidewire and through the guide catheter are minimized or eliminated. Instead, the anchored dilator described herein is anchored to the medical device (e.g., guide catheter, guide sheath, therapeutic or diagnostic catheter) and optionally directly delivered over the guidewire to the specified vascular location as a composite assembly. After the catheter is delivered, the dilator tip is transitioned to the shuttle configuration (e.g., the anchor cuff is compressed or relaxed) having a shuttle profile less than the lumen profile of the catheter. The dilator is readily withdrawn through the catheter delivery lumen, and optionally sterilized for future procedures. Further, because the anchored dilator is coupled to the medical device (either of the sheaths, catheters or the like described herein) for delivery to the specified vascular location the full profile of the vessel is available for the instrument without an intervening introducer sheath or the like that otherwise subtracts at least some of the vessel profile for later delivery of medical devices through a delivery lumen. Accordingly, access through smaller vessels, for instance in transradial approaches, is permitted with instruments that are otherwise too large when used with an introducer sheath and guide catheter and guide sheath. In some examples, instruments, catheters or the like typically used in femoral approach procedures are available for use in transradial approaches (e.g., through the wrist) with the anchored dilator system described herein.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
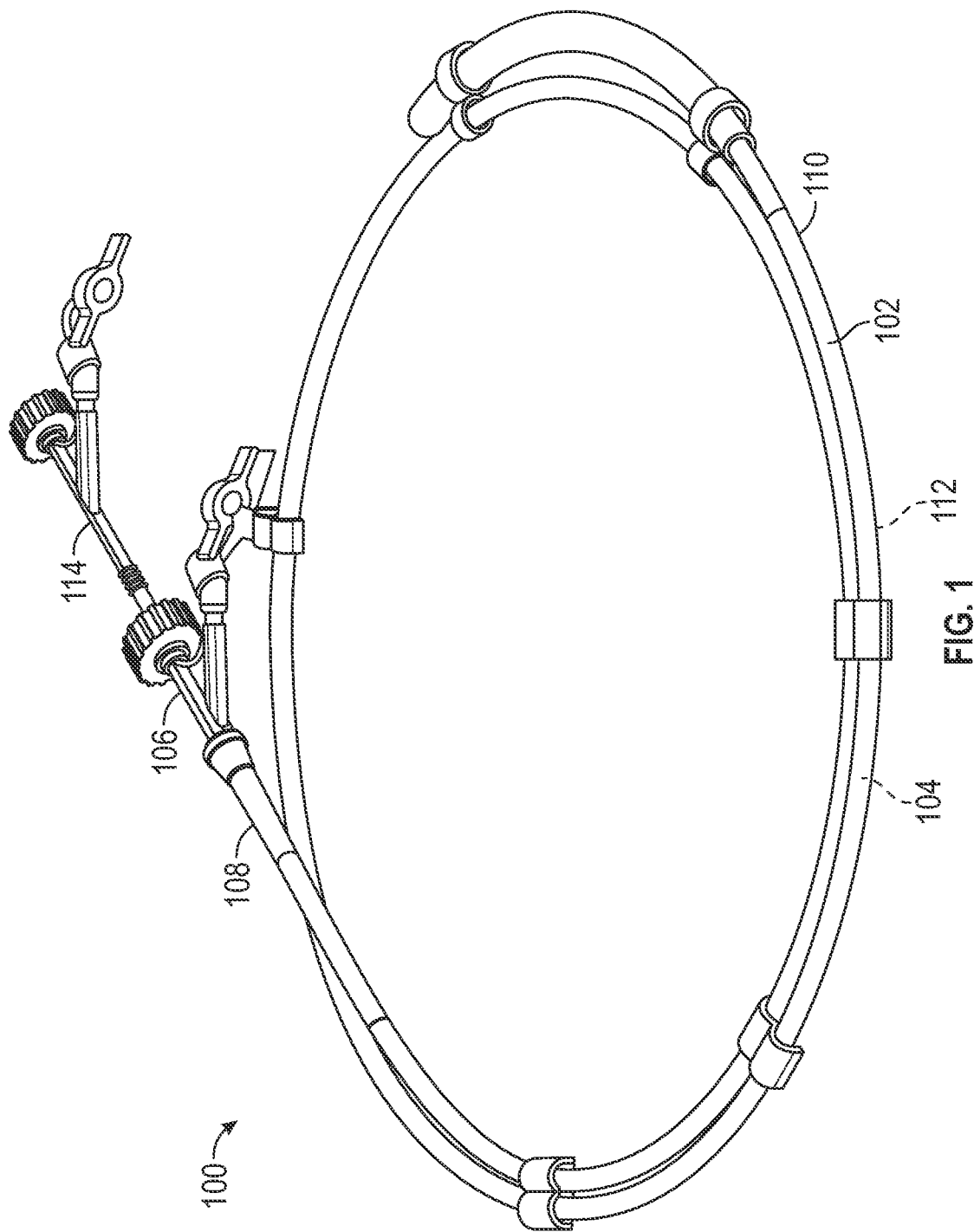
FIG. 1 is a perspective view of one example of one example of an anchored dilator system.

FIG. 1 is a perspective view of one example of an anchored dilator system 100. As shown, the system 100 includes a guide catheter 102 (e.g., including a guide catheter or other medical device having a lumen, such as a therapeutic instrument, diagnostic instrument or the like) connected with a hub assembly 106 proximate to a proximal catheter portion 108 of the guide catheter 102. The anchored dilator system 100 includes an anchored dilator 104 within a catheter lumen 112 (e.g., a delivery lumen) of the guide catheter 102. In this example, the anchored dilator 104 includes a dilator hub assembly 114 at a proximal portion of the dilator 104 and proximate to the hub assembly 106 of the guide catheter 102.

As shown in FIG. 1, the guide catheter 102 extends from the hub assembly 106. The anchored dilator 104 extends from the dilator hub assembly 114 through the catheter lumen 112 of the guide catheter 102, for instance, to a distal tip described herein. In one example, the distal tip is stored within the guide catheter 102 prior to use. For example, the distal tip of the anchored dilator 106 is held in a shuttle configuration (described herein) within a distal catheter portion 110 of the guide catheter 102 prior to use.

As described herein, the anchored dilator 104 is configured to transition between shuttle and anchored configurations to provide a tapered transition between the guide catheter 102 (including other medical devices) and the dilator 104. As described herein the anchored dilator 104 in combination with the guide catheter 102 is a unitary assembly that eliminates a separate introducer or introducer sheath, for instance, to provide an intermediate passage for one or more of the dilator, guide catheter or the like. Instead, the anchored dilator 104 directly positions the guide catheter 102 or other medical device at a specified target location within a vessel, cavity or the like through manipulation of the anchored dilator 104 to navigate the dilator and the guide catheter 102 attached to the dilator to the specified target location.

Figure 2:
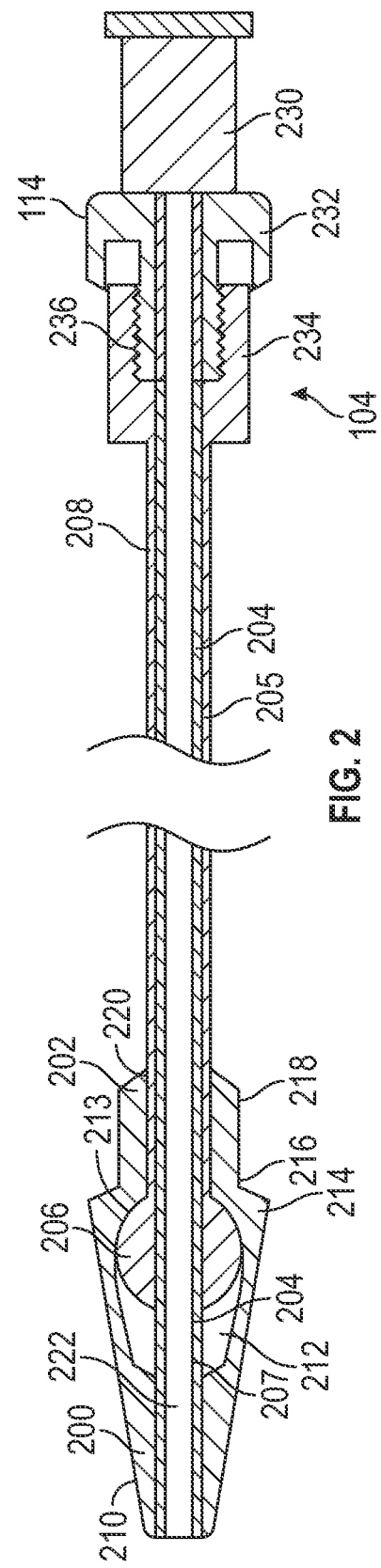
FIG. 2 is a sectional view of one example of an anchored dilator.

FIG. 2 shows a cross sectional view of one example of an anchored dilator 104, such as the anchored dilator shown in FIG. 1. In this example, the anchored dilator 104 extends from the dilator hub assembly 114 to the dilator tip 200. The dilator hub assembly 114 includes a dilator hub 232 and an operator hub 234. The anchored dilator 104 includes a push tube 204 extending from the dilator hub 232 to the dilator tip 200. For instance, in this example, the push tube 204 is an interior element relative to an operator shaft 208 that surrounds the push tube 204. As shown in FIG. 2, the push tube 204, in this example, is coupled with the dilator hub 232 with an adhesive, mechanical interfit, interference fit or the like. The push tube 204 extends from the dilator hub 232 to the dilator tip 200, and in an example includes a push tube lumen 222 to facilitate the passage of a guidewire, stylet or the like through the anchored dilator 104. The push tube 204 extends through a cuff operator 206 of the operator shaft 208 and extends through a portion of the dilator nose 210 of the dilator tip 200. For instance, a distal push tube portion 207 of the push tube 204 extends through the operator cavity 212 and is coupled with the dilator tip 200. Conversely, the proximal push tube portion 205 is coupled with the dilator hub 232 (e.g., with an adhesive, mechanical interfit, interference fit or the like).

Referring again to FIG. 2, the dilator tip 200 in this example includes an operator cavity 212 surrounded by a cavity surface 213. As described herein, in one example, the cavity surface 213 includes a tapered portion, for instance a portion of the cavity surface 213 proximate to the cuff operator 206, to facilitate deflection of one or more components of the dilator tip 200 such as the anchor cuff 202. Deformation of the anchor cuff 202 transitions the dilator tip 200 from the shuttle configuration shown in FIG. 2 to the deployed or anchored configuration shown, for instance, in FIG. 3B. Additionally, deployment of the anchor cuff 202 provides an affirmative anchoring engagement between the dilator tip 200 and the guide catheter 102 (or other medical device) to unify the anchored dilator 104 with the guide catheter 102 and facilitate navigation of vessels, cavities or the like as a composite unified assembly.

As further shown in FIG. 2, the dilator tip 200 further includes a pliable cuff interface 216 providing an interface between the anchor cuff 202 and the remainder of the dilator tip 200. In one example, the pliable cuff interface 216 is constructed with or includes a pliable or deformable material configured expand or outwardly deploy relative to the configuration shown in FIG. 2. The anchor cuff 202 is proximate to the pliable cuff interface 216 and the dilator transition 214. Optionally, the anchor cuff 202 includes a pliable or deformable material like the cuff interface. Pliable or deformable materials for one or more of the anchor cuff 202, dilator transition 214 and the pliable cuff interface 216 include, but are not limited to, polymers, elastomers or the like, such as rubber, silicone, polyvinyl chloride.

Referring again to FIG. 2, the anchor cuff 202 includes a cuff inner wall 220 extending around the push tube 204 and the operator shaft 208. The anchor cuff 202 further includes a cuff outer wall 218 providing the exterior surface, perimeter, profile or the like of the anchor cuff 202. As described herein, transitioning of the anchor cuff 202 from the shuttle to the anchored configuration biases the pliable cuff interface 216 from the shuttle configuration shown in FIG. 2 to the anchored configuration shown in FIG. 3B. Accordingly, at least a portion of the cuff outer wall 218 proximate to the pliable cuff interface 216 is deployed outwardly into engagement with one or more surfaces, features or the like of a catheter or other medical device, such as the guide catheter 102. In the deployed configuration, the dilator transition 214, in one example, provides a flush (including near flush, smooth or the like) transition from the dilator tip 200 to the medical device. For example, the dilator transition 214 provides a smooth transition from the tapered profile of the dilator nose 210 to the corresponding exterior surface of the medical device coupled with the anchored dilator 104 in the anchored configuration, such as the guide catheter 102. The smooth transition from the dilator nose 210 to the guide catheter 102 minimizes sharp corners, terraces, recesses or the like, and thereby facilitates navigation through vessels and cavities without engagement or snagging of tissues.

As further shown in FIG. 2, a cuff operator 206 is coupled with the dilator tip 200. The cuff operator 206 is moveable relative to the dilator tip 200, for instance through actuation of the operator shaft 208. In the example shown in FIG. 2, the cuff operator 206 includes an operator bulb, collet, jack or the like configured to deform a portion of the dilator tip 200, such as the pliable cuff interface 216, and deploy the anchor cuff 202 into the anchored configuration. The shape of the cuff operator 206 is tapered in one example and engages with a converse taper of the cavity surface 213. Engagement between the opposed tapers biases the pliable cuff interface 216 and the anchor cuff 202 into the anchored configuration with proximal movement of the cuff operator 206 from the position shown in FIGS. 2 (and 3A) to a position shown in FIG. 3B.

In one example, movement of the cuff operator 206 is remotely conducted by way of an operator drive 236 and the interposed operator shaft 208 extending from the operator hub 234 of the drive 236 to the cuff operator 206. As shown in FIG. 2, the operator drive 236 is optionally provided as a component of the dilator hub assembly 114. The operator drive 236 moveably interfits each of the dilator hub 232 and the operator hub 234 to facilitate movement of the cuff operator 206 relative to the dilator tip 200. In one example, the operator drive includes, but is not limited to, one or more of a ratchet engagement, threaded engagement or the like optionally providing one or more of haptic or audible feedback. The operator drive 236 includes haptic or audible feedback to indicated movement of the operator drive 236 and the cuff operator 206 and corresponding transition of the anchor cuff 202 between the shuttle and anchored configurations. In another example, the operator drive 236 includes one or more bearings to facilitate the movement of one or more of the operator hub 234 relative to the dilator hub 232. In one example, bearings interposed between the dilator hub 232 and the operator hub 234 include thrust bearings, roller bearings or the like.

As further shown in FIG. 2, a luer fitting 230 is, in one example, coupled with and in communication with the push tube lumen 222 of the push tube 204. The luer fitting 230 facilitates the delivery of one or more instruments such as guidewires, stylets or the like through the luer fitting 230 and into the push tube lumen 222. The dilator tip 200 is delivered over the guidewire, stylets or the like, for instance, by back loading of the dilator tip 200 onto the guidewire or stylet. The guidewire or stylet passes through the distal push tube portion 207 into the push tube lumen 222 and exits the anchored dilator 104 through the luer fitting 230.

Figure 3A:
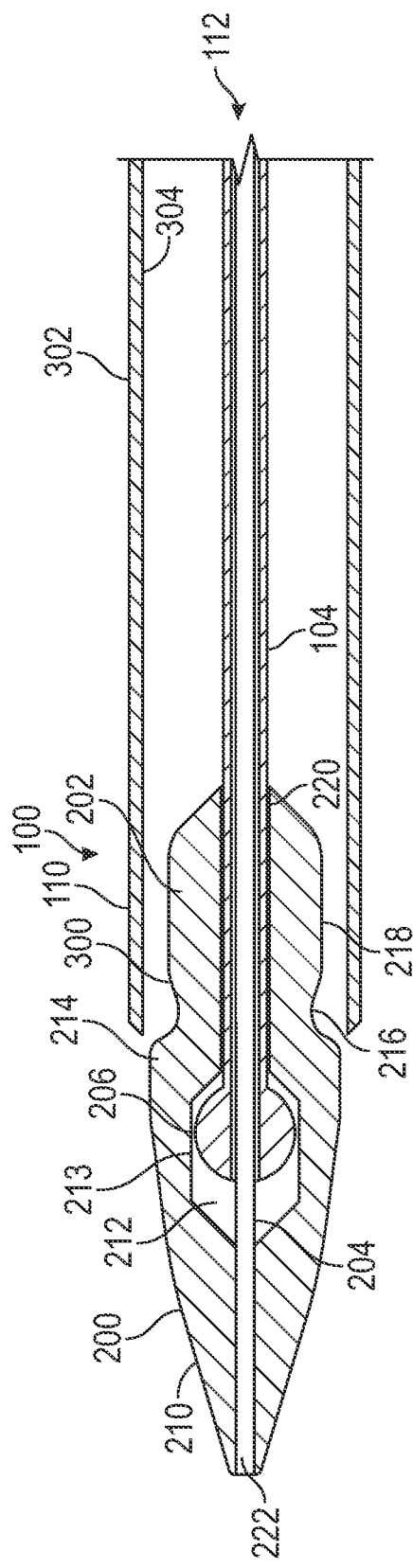
FIG. 3A is a sectional view of one example of a dilator tip in a shuttle configuration.
Figure 3B:
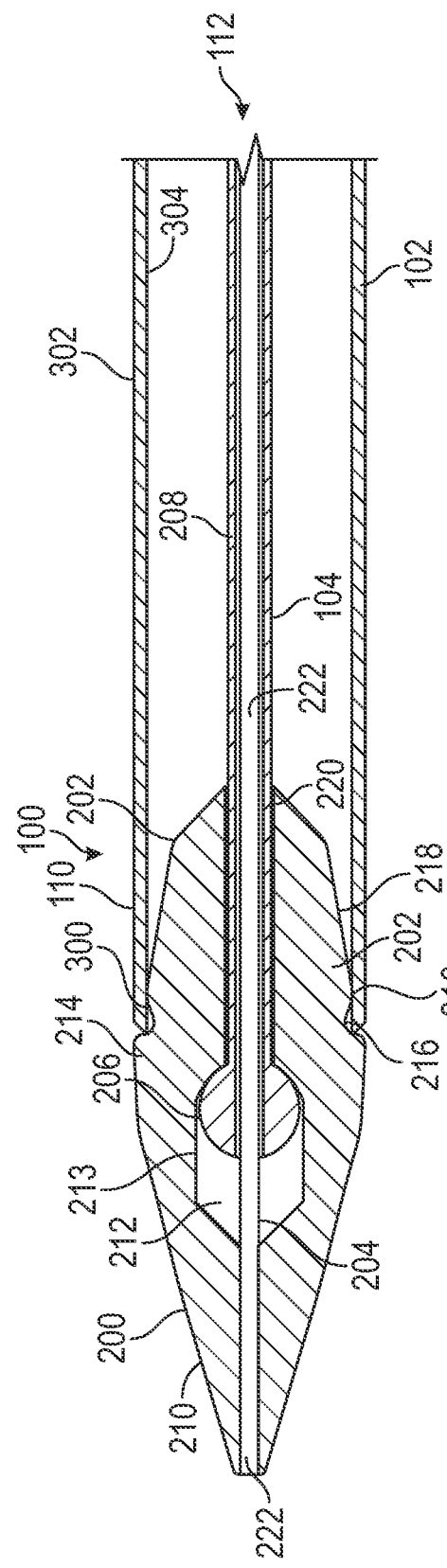
FIG. 3B is a sectional view of the dilator tip of FIG. 3A in an anchored configuration.

FIGS. 3A and 3B show two examples of the anchored dilator system 100 including the anchored dilator 104 and a medical device, such as a guide catheter 102. As shown in FIG. 3A, the anchor cuff 202 has a shuttle profile (e.g., a shuttle configuration) configured to pass through the guide catheter 102. Conversely, FIG. 3B shows the anchor cuff 202 of the anchor dilator 104 in a deployed or anchored configuration with the dilator tip 200 anchored with the catheter 102, for instance, a guide catheter 102 or other medical device, such as a guide sheath, therapeutic or diagnostic medical device or the like.

Referring first to FIG. 3A, as previously described, the dilator tip 200 having the anchor cuff 202 is in a shuttle configuration with a shuttle profile 300 smaller than an anchored profile 310 shown in FIG. 3B. The shuttle profile 300, in this example, is smaller than an interior surface 304 of the catheter 102 (e.g., a lumen profile). The dilator tip 200, push tube 204 and the operator shaft 208 are readily moved through the catheter 102, for instance, through proximal or distal loading of the dilator tip 200. As further shown in FIG. 3A, the dilator transition 214, cuff interface 216 and cuff outer wall 218 are recessed relative to the interior surface 304 of the catheter 102. The cuff operator 206 in the operator cavity 212 is spaced from one or more portions of the cavity surface 213 including, for instance, a proximal tapered portion of the cavity surface 213.

Referring now to FIG. 3B, the anchored dilator system 100 is in an anchored configuration, for instance, with the anchor cuff 202 deployed and engaged with the catheter 102. As shown, the cuff operator 206 is withdrawn or moved proximally relative to the position shown in FIG. 3A. The operator drive 236 shown in FIG. 2 is operated to move the cuff operator 206. For instance, the operator hub 234 is moved relative to the dilator hub 232. In an example including a threaded engagement between the hubs 232, 234, rotation of the operator hub 234 moves the hub 234 proximally, and also moves the operator shaft 208 and the cuff operator 206 proximally. The moved cuff operator 206 engages with the cavity surface 213 and deforms the cavity surface 213 and corresponding portions of the anchor cuff 202. For instance, as shown in FIG. 3B, the cuff interface 216 as well as the cuff outer wall 218 proximate to the interface 216 are biased outwardly and accordingly engage with the interior surface 304 of the catheter 102. The anchor cuff 202 has an anchored profile 310 larger than the shuttle profile 300 previously shown in FIG. 3A. One or more of the cuff interface 216 or the cuff outer wall 218 engage with the interior surface 304 of the guide catheter 102 to accordingly join the dilator tip 200 with the catheter 102 and form a unitary composite device.

Optionally, the anchor cuff 202 includes one or more features configured to enhance anchoring with the guide catheter 102 or other medical device. For instance, the cuff outer wall 218 includes one or more of a roughened texture, knurling, studs, ridges or the like that enhance engagement of the anchor cuff 202 with the interior surface 304 of the guide catheter 102. In another example, the anchor cuff 202 includes a tacky interface (e.g., in the manner of a rubber like surface, adhesive or the like) that enhances engagement between the anchor cuff 202 and the interior surface 304 of the guide catheter.

As further shown in FIG. 3B, the dilator transition 214 is proximate to an end of the catheter 102 (e.g., a distal catheter portion 110 as shown in FIGS. 1 and 3B). As shown, the dilator transition 214, when deployed in the anchored configuration, smoothly transitions the dilator nose 210 to the exterior surface 302 of the catheter 102. For example, the dilator transition 214 provides a flush (including near flush) transition between the exterior surface 302 of the catheter 102 and the dilator nose 210. The dilator transition 214 in the anchored configuration provides a continuous interface from the dilator nose to the catheter 102 to facilitate delivery of the dilator 104 and catheter 102 through vasculature. Additionally, the dilator transition 214 conceals and isolates the edge of the catheter 102 (e.g., a distal edge of the guide catheter) to minimize risk of trauma through razoring of a vessel or collision with tissues. Accordingly, the dilator transition 214 of the dilator tip 200 minimizes snags, sharp corners, exposed edges or the like that otherwise, in some examples, snag or roughly engage with tissues.

The anchored dilator system 100 including the catheter 102 (e.g., a guide catheter, guide sheath or other medical device) and the deployed anchored dilator 104 are a unitary device that facilitates the navigation of the system 100 through vasculature and to a specified location. In one example, the operator navigates the system 100 through the vasculature through manipulation (e.g., pushing, pulling, rotation or the like) of one or more of the catheter 102 or the anchored dilator 104. For instance, the system 100 is moved in a unitary manner through manipulation of the catheter 102 and corresponding movement of the deployed anchored dilator 104. In another example, the push tube 204 of the anchored dilator 104 is manipulated (e.g., pushed, pulled, rotated or the like) and navigates both of the dilator tip 200 and the deployed anchor cuff 202. The catheter 102 is coupled with the anchored dilator 104 with the deployed anchor cuff 202 and thereby correspondingly moves with manipulation through the push tube 204.

In an example, the catheter 102 is a guide catheter including one or more bracing features such as a braid, coil, structural wall or the like in comparison to more pliable devices, such as guide sheaths. A guide catheter 102 is in some examples specified for access to a vascular location. In other procedures an intermediate sheath, such as a guide sheath, introducer sheath or guide sheath in combination with an introducer sheath, are previously navigated through vasculature to provide a conduit for the guide catheter. The sheaths facilitate the passage of the guide catheter and minimize risks including razoring of vessel walls, tissues or the like through engagement of the edge of the guide catheter with the walls or tissues. The introducer sheath, guide sheath or combination of sheaths subtracts from vascular space otherwise available for the guide catheter or other medical device. In an example including the anchor dilator 104, the system 100 of the anchored dilator and the guide catheter 102 is readily navigated through the vasculature without an intervening sheath (introducer sheath, guide sheath or the like). Instead, the deployed anchor cuff 202 engages with the surfaces of the guide catheter 102 proximate to the distal end and conceals and isolates edges of the guide catheter 102 that may, in some examples, increase the risk of trauma to organs, tissues, vessel walls or the like. The anchored dilator system 100 including the anchored dilator 104 provides a tapered, smooth composite assembly that is readily navigated by itself through the vasculature.

After delivery of the anchored dilator system 100, for instance, to a specified location of the vasculature, the anchored dilator 104 is optionally decoupled from the catheter 102 (including one or more of a guide catheter, therapeutic medical device or the like) and removed, for instance, through the catheter lumen 112 shown in FIG. 3B. In this example, the operator drive 236 (FIG. 2) is operated in reverse to transition the anchor cuff 202 from the anchored configuration to the shuttle configuration. Rotation or movement of the operator drive 236 moves the operator hub 234 relative to the dilator hub 232. In this example, the operator hub 234 is moved distally. The operator shaft 208 connected to the operator hub 234 moves distally and thereby distally moves the cuff operator 206 from the position shown in FIG. 3B to the position shown in FIG. 3A with the operator 206 decoupled (including a relaxed engagement) with the cavity surface 213. Decoupling of the cuff operator 206 (including relaxed engagement) relative to the cavity surface 213 relaxes the anchor cuff 202 and allows the anchor cuff 202 to compress to the shuttle configuration shown in FIG. 3A. As the anchor cuff 202 relaxes and resumes the shuttle configuration, the dilator transition 214 as well as the cuff outer wall 218 withdraw relative to the interior surface 304 of the catheter 102 thereby reducing the profile of the anchor cuff 202 to the shuttle profile 300 and facilitating the withdrawal of the dilator tip 200 through the catheter 102.

Figure 4:
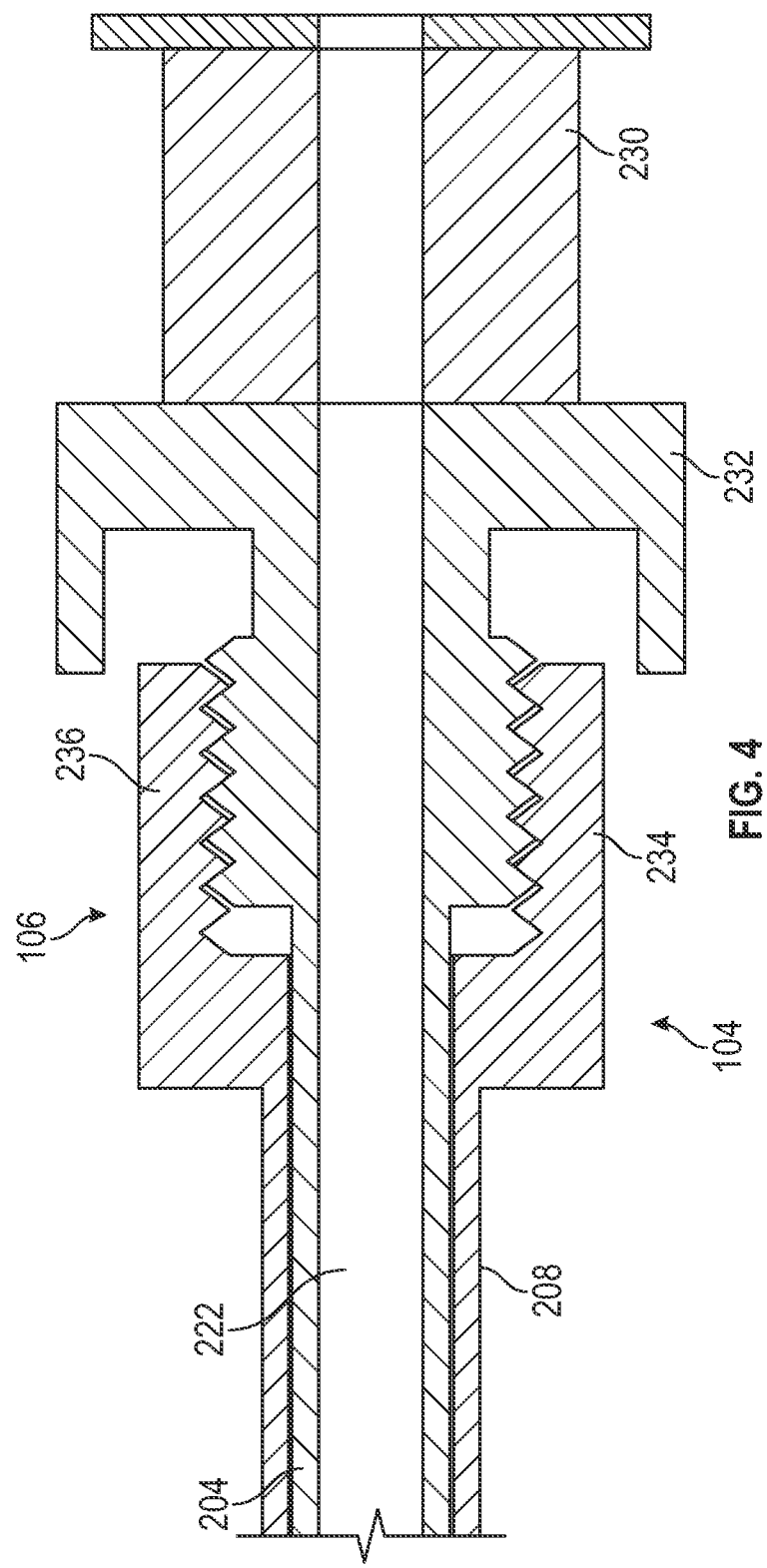
FIG. 4 is a sectional view of one example of an operator drive.

FIG. 4 is a cross sectional view of one example of the operator drive 236. In this example, the operator drive 236 includes a threaded engagement between the dilator hub 232 and the operator hub 234. Movement of the operator drive 236 transitions the operator, such as the cuff operator 206 shown in FIGS. 3A, 3B, between proximal and distal positions that correspond to the anchored and shuttle configurations previously described herein.

In the example shown in FIG. 4, the dilator hub 232 is coupled along an interior portion of the operator hub 234. The dilator hub 232 is connected with the push tube 204 extending toward the distal push tube portion 207 shown, for instance, in FIG. 2. The distal push tube portion 207 is coupled with the dilator nose 210 of the dilator tip 200. The push tube 204 extending between the dilator nose 210 and the dilator hub 232 accordingly provides a relatively robust component for the anchor dilator 104 to facilitate the pushing movement of the dilator nose 210 as well as one or more components anchored to the dilator tip 200, such as the catheter 102 described herein. Pushing movement delivered along the push tube 204 to the dilator nose 210 correspondingly pulls the anchored instrument coupled with the dilator tip 200 into the vasculature. As further shown in FIG. 4, the push tube 204 is provided, in this example, along an interior of the operator shaft 208. The push tube lumen 222 is provided along an interior of the push tube 204 for delivery or passage of guidewires, stylets or the like.

As further shown in FIG. 4, the operator drive 236 includes an operator hub 234 movably coupled (e.g., a threaded, ratchet coupling or the like) with the dilator hub 232. The operator hub 234 is, in turn, coupled with the operator shaft 208 extending, in this example, around the push tube 204. Movement of the operator hub 234 moves the operator shaft 208 and cuff operator 206 and transitions the cuff operator between the shuttle and anchored configurations shown in FIGS. 3A, 3B. Accordingly, movement of the cuff operator 206 by the operator hub 234 remotely transitions the dilator tip 200 including its anchor cuff 202 between the shuttle and anchored configurations.

In the example shown in FIG. 4, the operator drive 236 includes a threaded interface between the dilator hub 232 and the operator hub 234. In other examples, the operator drive 236 includes a ratchet engagement, rack and pinion type engagement or the like configured to provide predictable graduated movement of the operator hub 234 and the cuff operator 206. In the example shown in FIG. 4, rotation of the operator hub 234 moves the operator hub proximally or distally (depending on the direction of rotation) and correspondingly moves the operator shaft 208 and the associated cuff operator 206. Rotation of the operator hub 234 in a clockwise direction, in one example moves the operator shaft 208 and the cuff operator 206 proximally thereby engaging the cuff operator with the cavity surface 213 of the dilator tip 200 and deforming the anchor cuff 202 into the anchored configuration shown in FIG. 3B. Conversely, rotation in an opposed direction, such as the counterclockwise direction, moves the operator hub 234, the operator shaft 208 and the cuff operator 206 distally. The cuff operator 206 relaxes its engagement or disengages from the cavity surface 213. Accordingly, the anchor cuff 202 transitions from the anchored configuration shown in FIG. 3B to the shuttle configuration shown in FIG. 3A.

In still other examples, the operator drive 236 includes one or more features configured to provide haptic (tactile) or audible feedback to a clinician, technician or the like. For instance, as the operator drive 236 is actuated the cuff operator 206 moves and the drive generates ticks, clicking or the like in one or more of a tactile or audible manner. The feedback provides notification to the clinician or technician of the graduated movement, and the magnitude of the movement (e.g., based on the number of ticks or clicks heard or felt).

In still other examples, the operator drive 236 includes one or more features such as bearings, lubricants or lubricious coatings or materials configured to constrain movement of the operator hub 234, dilator hub 232 and the associated operator shaft 208 and push tube 204 to rotational movement without axial loading. For instance, in one example, bearings, lubricants or the like are provided between one or more of the push tube 204 and operator shaft 208 to limit twisting motion otherwise applied to the push tube 204, for instance with rotation of the operator shaft 208. Conversely, one or more of thrust bearings, rotational bearings, lubricants or the like, in another example, are configured to limit or constrain movement between the operator hub 234 and the dilator hub 232 (as well as the associated shaft and tube 208, 204) to rotation and specified axial movement to actuate the anchor cuff 202, and thereby limit additional axial movement transmitted between the components.

Figure 5:
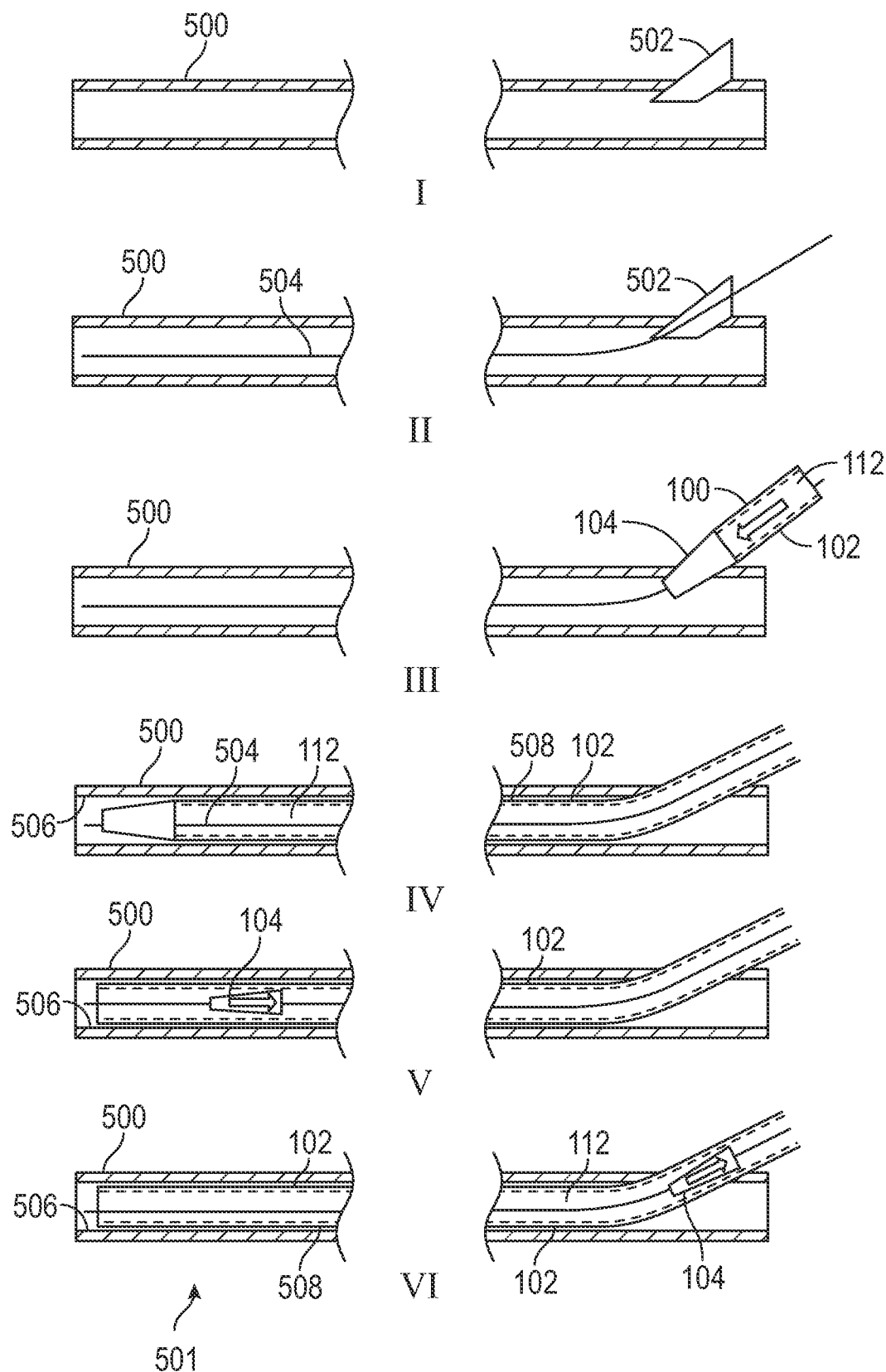
FIG. 5 is a schematic view of one example method of device delivery including an anchored dilator.

FIG. 5 shows one example of a device delivery method 501 including the anchored dilator 104 previously described herein. FIG. 5 is divided into six portions (denoted with roman numerals) each corresponding to an example step for the delivery of a medical device, such as the guide catheter 102 or other medical device, to a specified target location in a vessel 500. As shown in FIG. 5, the anchored dilator system 100 is navigated to the specified vascular location without an introducer sheath, guide sheath or the like. Instead, the anchored dilator 104 is deployed and engages with the guide catheter 102 for navigation of the system 100 to the location. Referring first to step I, a needle 502 penetrates the vessel 500 to provide access to the interior of the vessel 500. As shown in portion 11, the needle 502 remains within the vessel 500 and a guidewire 504 is fed through the needle 502, for instance, to the specified location of the vessel 500 shown in FIG. 5 as the leftmost portion of the vessel.

As further shown in FIG. 5, for instance, in portion III, the anchored dilator system 100 including the anchored dilator 104 coupled with the guide catheter 102 is administered through the penetration of the vessel 500. For example, the anchored dilator 104 is loaded into the guide catheter 102 or other medical device, for instance through the catheter lumen 112, as previously described herein. The anchored dilator 104 is transitioned to the anchored configuration through actuation of the anchor cuff 202, to anchor the dilator tip 200 to a corresponding portion of the guide catheter 102 (e.g., proximate to a distal end of the catheter). In this arrangement, the anchored dilator 104 and the guide catheter 102 are a unified composite body that is delivered along the guidewire 502 and into the vessel 500. Additionally, the anchored dilator 104 conceals and isolates the edge of the guide catheter 102 (e.g., the edge surrounding the distal opening of the catheter) and thereby minimizes the risk of trauma from the edge while at the same time provide a tapered and smooth profile for the system 100.

As shown in portion IV, the composite assembly of the guide catheter 102 and the anchored dilator 104 (one example of an anchored dilator system 100) is delivered through the vessel 500 with the dilator 104 leading the guide catheter 102 through the vessel 500. As previously described, the anchored dilator 104 includes a dilator tip 200 that tapers toward the dilator nose 210 to facilitate passage of the guide catheter 102 through the vessel 500. The cuff operator 206 expands the anchor cuff 202 and an associated optional dilator transition tube 214. The expanded dilator transition 214 is in close correspondence with a proximate portion of the guide catheter 102. As shown in FIG. 3B, the deployment of the anchor cuff 202 and the dilator transition 214 into the anchored configuration provides a flush (including near flush) transition from the dilator tip 200 to the exterior surface 302 of the guide catheter 102. Accordingly, one or more of steep transitions, corners, steps or the like are accordingly minimized at the interface between the dilator tip 200 and the exterior surface 302 of the guide catheter 102 to provide a smooth transition between the dilator tip 200 and the guide catheter 102 and minimize snagging, rough engagement or the like with the tissues of the vessel 500.

Referring now to portion IV of FIG. 5, the dilator 104 in the anchored configuration is delivered through the vessel 500, for instance, by way of axial force applied to the dilator 104 by way of the push tube 204 shown in FIG. 2. The push tube 204 is not shown in FIG. 5 to facilitate viewing of other components of the anchored dilator system 100. Axial force applied along the push tube 204 is delivered to the dilator tip 200. The axially pushed dilator tip 200 coupled with the proximate portion of the guide catheter 102 or other medical device accordingly pulls the guide catheter 102 through the vessel 500 to the specified vessel location.

As further shown in portion IV of FIG. 5, the guide catheter 102 or other medical device has a device profile 508. As shown, the device profile 508 is a shape, size or the like of the guide catheter 102. In this example, the device profile 508 of the guide catheter 102 substantially corresponds with a vessel profile 506 (e.g., shape, size or the like) of the vessel 500. For instance, the diameter, shape or the like of the guide catheter 102 or other medical device substantially matches that of the vessel 500. Accordingly as shown in portions IV, V and VI, the guide catheter 102 having the device profile 508 readily delivered to the specified location within the vessel 500.

Referring now to portion V of FIG. 5, the guide catheter 102 or other medical device is delivered to the specified location as previously shown in portion IV. After delivery of the guide catheter 102 to the specified location, the anchored dilator 104 is retracted to the shuttle configuration shown in FIG. 3A to facilitate its extraction from the vessel 500. For instance, as shown in portion V the anchored dilator 104 in the shuttle configuration has a smaller profile relative to the dilator 104 shown in portions III and IV in the anchored configuration. The cuff operator 206 is actuated to transition the anchor cuff 202 between the anchored configuration shown in FIG. 3B to the shuttle configuration shown in FIG. 3A. In the shuttle configuration the anchored dilator 104 is withdrawn along the guidewire 504 and (as shown in portion VI) removed from the guide catheter 102.

The guide catheter 102 or other medical device delivered with the anchored dilator 104 remains within the vessel 500. As shown, the catheter 102 has a device profile 508 substantially corresponding to the vessel profile 506. For example, the medical device having the device profile 508 fit to the vessel profile 506 is delivered to the specified location and left in place for one or more procedures. Because an introducer sheath or other intermediate device is not used with the anchored dilator 104 in the device delivery 501 minimal space in the vessel 500, otherwise used by an introducer sheath or the like, is instead available for larger guide catheters 102 or other medical devices.

Figure 6:
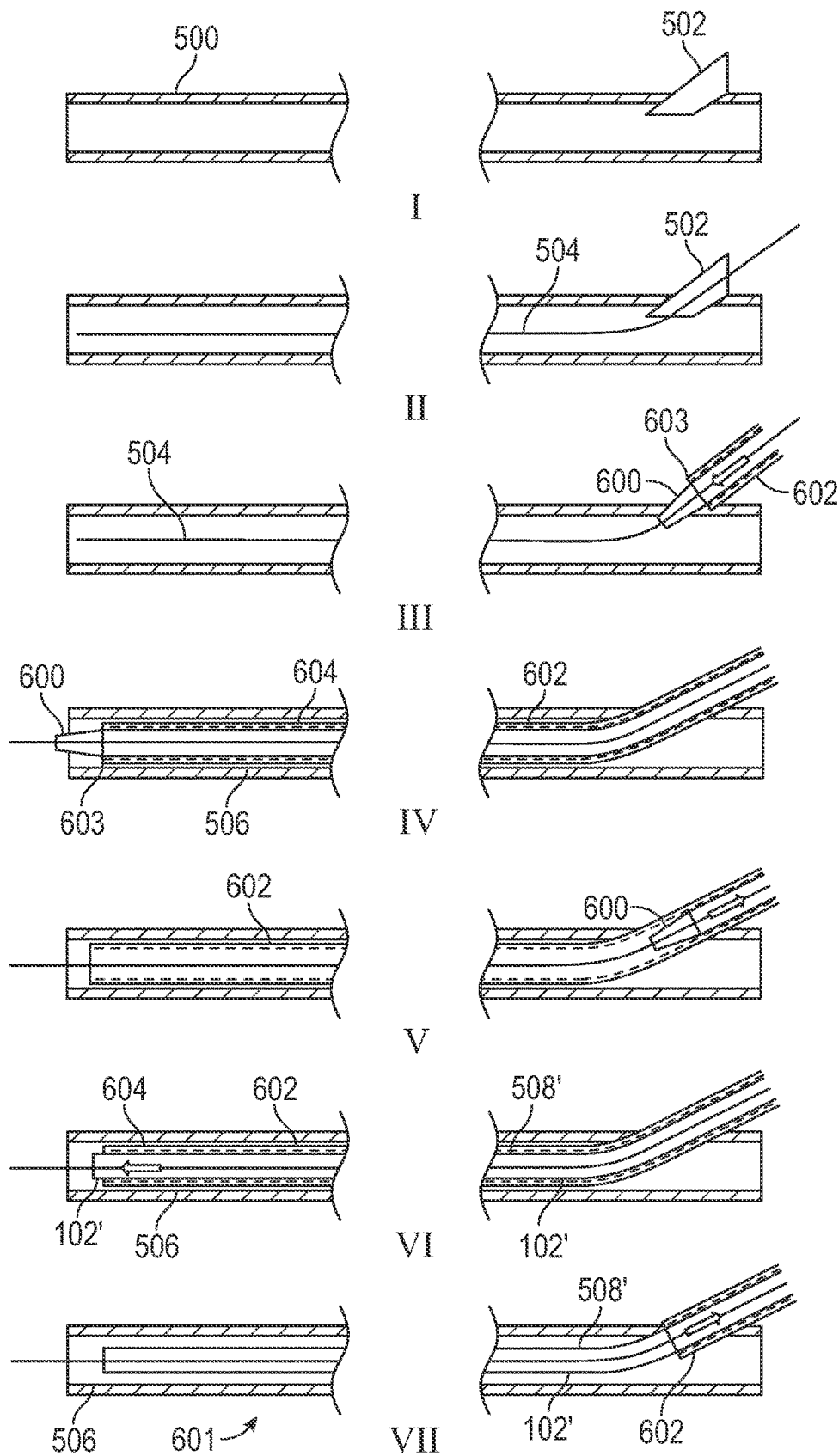
FIG. 6 is a schematic view of another example method of device delivery.

FIG. 6 shows another series of examples of a device delivery 601 including an introducer sheath 602. As described herein, in some example the delivery 601 further includes additional sheaths, such as guide sheaths or the like used alone or in combination with the introducer sheath 602. As shown, the device delivery 601 provided in FIG. 6 includes at least seven portions or steps. Referring first to portion I, the vessel 500 is shown with a needle 502 inserted through the vessel wall to provide access into the vessel 500 for delivery of one or more instruments therein. As shown in portion II, a guidewire 504 is inserted through the needle 502 and into the vessel 500, and navigated to a specified location within the vessel 500.

As shown in portion III, the guidewire 504 remains within the vessel 500. A dilator 600 is fed through an introducer sheath 602 and both the introducer sheath 602 and the dilator 600 are back loaded onto the guidewire 504 and introduced through the penetration of the needle into the vessel 500. As further shown in portion III, the dilator 600 is recessed from the interior wall of the introducer sheath 602 to allow for delivery through a delivery lumen of the sheath 602. Accordingly, an exposed edge 603 of the introducer sheath 602 is revealed. In other examples, multiple dilators 600 having gradually increasing sizes are navigated through the vessel 500 for dilation of the vessel in preparation for delivery of the introducer sheath 602.

As further shown in portion IV, the dilator 600 and introducer sheath 602 are moved together, for instance, through translation of corresponding hubs through the vessel 504. The dilator 600 provides an intermediate component between the guidewire 504 and the introducer sheath 602 to facilitate navigation through the vessel 500 and attempts to minimize trauma, such as razoring. However, as shown in portion IV the exposed edge 603 extends away from the dilator 600 and is revealed and proximate to the vessel walls. As shown in portion IV, the introducer sheath 602 has an introducer profile 604 substantially matching the vessel profile 506 of the vessel 500. As further shown in portion IV, the dilator 600 provides a transition to the introducer sheath 602 from the guidewire 504. In contrast to the anchored dilator 104 previously described herein, the dilator 600 extends through a lumen of the introducer sheath 602 and provides a stepped interface from the dilator 600 to the proximate distal portion of the introducer sheath 602.

Accordingly, the dilator 600 shown in FIG. 6, does not include the dilator transition 214, for instance, provided in the anchored configuration with the anchored dilator system 100 and the anchored dilator 104. The dilator transition 214 shown in FIG. 3B, for instance, provides a smooth transition from the dilator tip 200 to the proximate portion of the guide catheter 102 shown in FIG. 3B and thereby conceals the otherwise exposed edge of the guide catheter. For instance, the cuff operator 206 deploys or expands a portion of the dilator tip 200 such as the anchor cuff 202 in a close intimate engagement with an interior surface 304 of the guide catheter such as the guide catheter 102 shown in FIG. 3B. Additionally, the operation of the cuff operator 206 expands the anchor cuff 202 and correspondingly expands the dilator transition 214 to provide a flush or near flush transition from the dilator tip to the corresponding proximate portion of the guide catheter 102 that covers and isolates the edge of the guide catheter 102. In contrast to the smooth transition provided in FIG. 3B, the dilator 600 and introducer sheath 602 shown in FIG. 6 provide a stepped or staggered profile having the exposed edge 603 that may, in some circumstance, provide a rough engagement between the dilator 600, introducer sheath 602 and the corresponding portions of the vessel 500 that increases the risk of trauma, such as razoring.

As further shown in FIG. 6, for instance, in portion V, after deployment of the introducer sheath 602 to the specified target location, the dilator 600 is removed, for instance, by sliding movement of the dilator through the introducer sheath 602 and out of the penetration previously provided by the needle 502. As further shown in portion VI of FIG. 6, the introducer sheath 602 remains within the vessel 500 and one or more guide catheters, medical devices 102' or the like are delivered through the introducer sheath 602 to the specified location within the vessel 500. As shown in portion VI, the guide catheter or medical device 102' includes a device profile 508' configured to fit within the introducer sheath 602. The device profile 508' is accordingly smaller than the vessel profile 506 to facilitate delivery through the introducer sheath 602.

Referring now to portion VII of the device delivery 601 shown in FIG. 6, after delivery of the guide catheter or medical device 102' to the specified target location within the vessel 500, the introducer sheath 602 is, in one example, removed from the vessel 500, for instance, by drawing of the introducer sheath 602 over along the guidewire 504 and the medical device 102' and through the penetration previously provided in the vessel 500. The guide catheter or other medical device 102' remains within the vessel 500.

As shown, the guide catheter or medical device 102' includes the device profile 508' and the device profile 508' is smaller than the vessel profile 506 because of the previously interposed introducer sheath 602. Accordingly, in the example shown in FIG. 6, the device delivery 601 provides a smaller device 102' having a corresponding smaller device profile 508' in comparison to the device profile 508 shown, for instance, in FIG. 5 more closely corresponding to the vessel profile 506. As shown in FIG. 5, the anchored dilator 104 facilitates the delivery of the guide catheter or medical device 102 having the larger device profile 508 because the anchored dilator 104 is mated to and anchors with the guide catheter or medical device 102 and facilitates its delivery through the vessel 500 without a previously installed introducer sheath such as the introducer sheath 602 used in the device delivery 601 shown in FIG. 6. Instead, the guide catheter or medical device 102 shown in FIG. 5 is mated with the anchored dilator 104 and delivered as a unitary assembly through the vessel 500 to the specified target location. Additionally, the deployed anchor cuff 202 isolates otherwise exposed edges and minimizes the risk of trauma (e.g., razoring) through vessel navigation. After positioning of the guide catheter or medical device 102 at the specified target location, the dilator 104 is readily contracted into the shuttle configuration shown in FIG. 5 and previously shown and described in FIG. 3A. The contracted dilator 104 is withdrawn over the guidewire 504.

VARIOUS NOTES AND ASPECTS

Aspect 1 can include subject matter such as an anchored dilator system comprising: a guide catheter having proximal and distal catheter end portions and a catheter lumen extending therebetween; an anchored dilator received in the catheter lumen, the anchored dilator includes: a dilator tip having an anchor cuff; a push tube coupled with the dilator tip and extending toward the proximal catheter end portion; a cuff operator proximate the dilator tip; and an operator shaft coupled with the cuff operator, the operator shaft extends from the dilator tip toward the proximal catheter end portion; and wherein the anchor cuff is configured to transition between the anchored and shuttle configurations: in the anchored configuration actuation of the cuff operator with the operator shaft deploys the anchor cuff into engagement with the distal catheter end portion, and in the shuttle configuration the anchor cuff is withdrawn and disengaged with the distal catheter end portion.

Aspect 2 can include, or can optionally be combined with the subject matter of Aspect 1, to optionally include wherein the dilator tip includes a dilator nose distal to the anchor cuff, the dilator nose tapers distally from the anchor cuff toward the push tube.

Aspect 3 can include, or can optionally be combined with the subject matter of one or any combination of Aspects 1 or 2 to optionally include wherein the dilator includes a dilator transition proximate the anchor cuff, and in the anchored configuration the dilator transition is flush with an exterior surface of the guide catheter.

Aspect 4 can include, or can optionally be combined with the subject matter of one or any combination of Aspects 1-3 to optionally include wherein in the shuttle configuration the anchor cuff includes a shuttle profile, and in the anchored configuration the anchor cuff includes an anchored profile larger than the shuttle profile.

Aspect 5 can include, or can optionally be combined with the subject matter of one or any combination of Aspects 1-4 to optionally include wherein the shuttle profile is smaller than a lumen profile of the guide catheter, and the anchored profile is equal to or greater than the lumen profile.

Aspect 6 can include, or can optionally be combined with the subject matter of Aspects 1-5 to optionally include wherein the anchor cuff is a pliable anchor cuff, and the deployed anchor cuff in the anchored configuration includes an expanded anchor cuff.

Aspect 7 can include, or can optionally be combined with the subject matter of Aspects 1-6 to optionally include wherein the cuff operator includes an operator bulb coupled with the operator shaft.

Aspect 8 can include, or can optionally be combined with the subject matter of Aspects 1-7 to optionally include wherein the distal tip includes a cavity surface surrounding an operator cavity, and the cuff operator is received in the operator cavity.

Aspect 9 can include, or can optionally be combined with the subject matter of Aspects 1-8 to optionally include wherein at least a portion of the anchor cuff is proximate the cuff operator and the cavity surface, and the cavity surface includes a tapered interface.

Aspect 10 can include, or can optionally be combined with the subject matter of Aspects 1-9 to optionally include wherein in the anchored configuration the cuff operator is configured to engage the tapered interface and expandably deploy the tapered interface and the anchor cuff into engagement with an interior surface of the guide catheter.

Aspect 11 can include, or can optionally be combined with the subject matter of Aspects 1-10 to optionally include an anchored dilator comprising: a push tube having proximal and distal push tube portions; a dilator tip coupled with the distal push tube portion, the dilator tip is configured for selectable coupling with a catheter, the dilator tip includes: an anchor cuff having a cuff interface, the anchor cuff is configured to transition between a shuttle configuration having a shuttle profile and an anchored configuration having an anchored profile larger than the shuttle profile; and a dilator nose distal to the anchor cuff; and a cuff operator assembly configured to transition the anchor cuff between the anchored and shuttle configurations, the cuff operator assembly includes: a cuff operator movably coupled with the dilator tip; an operator shaft coupled with the cuff operator, the operator shaft extends toward the proximal push tube portion; and wherein actuation of the cuff operator with the operator shaft transitions the anchor cuff between the shuttle configuration and the anchored configuration.

Aspect 12 can include, or can optionally be combined with the subject matter of Aspects 1-11 to optionally include wherein the dilator nose tapers distally from the anchor cuff toward the push tube.

Aspect 13 can include, or can optionally be combined with the subject matter of Aspects 1-12 to optionally include wherein the dilator tip includes a dilator transition proximate the anchor cuff, in the shuttle configuration the dilator transition is proximate to the push tube, and in the anchored configuration the dilator transition is remote to the push tube relative to the shuttle configuration.

Aspect 14 can include, or can optionally be combined with the subject matter of Aspects 1-13 to optionally include wherein the anchor cuff is a pliable anchor cuff, and the anchor cuff in the anchored configuration includes an expanded anchor cuff.

Aspect 15 can include, or can optionally be combined with the subject matter of Aspects 1-14 to optionally include wherein the cuff operator includes an operator bulb coupled with the operator shaft.

Aspect 16 can include, or can optionally be combined with the subject matter of Aspects 1-15 to optionally include wherein the distal tip includes a cavity surface surrounding an operator cavity, and the cuff operator is received in the operator cavity.

Aspect 17 can include, or can optionally be combined with the subject matter of Aspects 1-16 to optionally include wherein the cavity surface includes a tapered interface, and in the anchored configuration the cuff operator is configured to deform the tapered interface and expand the anchor cuff to the anchored profile.

Aspect 18 can include, or can optionally be combined with the subject matter of Aspects 1-17 to optionally include wherein the cuff operator is in a distal position in the shuttle configuration, and in a proximal position in the anchored configuration.

Aspect 19 can include, or can optionally be combined with the subject matter of Aspects 1-18 to optionally include wherein the cuff operator is slidably coupled along the push tube.

Aspect 20 can include, or can optionally be combined with the subject matter of Aspects 1-19 to optionally include wherein the operator shaft is slidably coupled along the push tube.

Aspect 21 can include, or can optionally be combined with the subject matter of Aspects 1-20 to optionally include a hub assembly proximate the proximal push tube portion, the hub assembly includes: a dilator hub coupled with the proximal push tube portion; and an operator hub coupled with a proximal shaft portion of the operator shaft.

Aspect 22 can include, or can optionally be combined with the subject matter of Aspects 1-21 to optionally include wherein the hub assembly includes an operator drive interposed between the dilator hub and the operator hub, and the operator drive is configured to actuate the operator shaft, move the cuff operator and transition the anchor cuff between the shuttle and anchored configurations.

Aspect 23 can include, or can optionally be combined with the subject matter of Aspects 1-22 to optionally include wherein the operator drive includes a threaded interface between the dilator hub and the operator hub.

Aspect 24 can include, or can optionally be combined with the subject matter of Aspects 1-23 to optionally include a method for using an anchored dilator system comprising: passing a dilator having a dilator tip coupled with a push tube through a catheter lumen of a catheter, an interior surface of the catheter surrounds the catheter lumen; and anchoring the dilator tip with the catheter with an anchor cuff, anchoring the dilator tip includes: passing a dilator nose of the dilator tip past a distal catheter portion of the catheter; delivering the anchor cuff of the dilator tip toward the distal catheter portion through the catheter lumen, the anchor cuff in a shuttle configuration having a shuttle profile smaller than a lumen profile of the catheter; transitioning the anchor cuff from the shuttle configuration to an anchored configuration, the anchor cuff in the anchored configuration having an anchored profile larger than the shuttle profile; and engaging the anchor cuff in the anchored configuration with the interior surface of the catheter.

Aspect 25 can include, or can optionally be combined with the subject matter of Aspects 1-24 to optionally include delivering the catheter and the dilator tip to a specified vascular location.

Aspect 26 can include, or can optionally be combined with the subject matter of Aspects 1-25 to optionally include wherein delivering the catheter and the dilator tip includes: manipulating the dilator tip with the push tube; and guiding movement of the catheter with the dilator tip having the anchor cuff in the anchored configuration and engaged with the interior surface of the catheter.

Aspect 27 can include, or can optionally be combined with the subject matter of Aspects 1-26 to optionally include wherein transitioning the anchor cuff from the shuttle configuration to the anchored configuration includes expanding the anchor cuff.

Aspect 28 can include, or can optionally be combined with the subject matter of Aspects 1-27 to optionally include wherein the anchor cuff includes a pliable anchor cuff, and transitioning the anchor cuff from the shuttle configuration to the anchored configuration includes deforming the anchor cuff.

Aspect 29 can include, or can optionally be combined with the subject matter of Aspects 1-28 to optionally include wherein the distal tip includes a cuff operator coupled with an operator shaft, and transitioning the anchor cuff from the shuttle configuration to the anchored configuration includes: moving the cuff operator toward the anchor cuff with the operator shaft; and biasing the anchor cuff into the anchored configuration with the cuff operator.

Aspect 30 can include, or can optionally be combined with the subject matter of Aspects 1-29 to optionally include wherein engaging the anchor cuff with the interior surface of the catheter includes engaging the anchor cuff in surface to surface contact with the interior surface of the catheter proximate to the distal catheter portion.

Aspect 31 can include, or can optionally be combined with the subject matter of Aspects 1-30 to optionally include wherein transitioning the anchor cuff from the shuttle configuration to the anchored configuration includes blending a dilator nose of the dilator tip with an exterior surface of the guide catheter.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "aspects" or "examples." Such aspects or example can include elements in addition to those shown or described. However, the present inventors also contemplate aspects or examples in which only those elements shown or described are provided. Moreover, the present inventors also contemplate aspects or examples using any combination or permutation of those elements shown or described (or one or more features thereof), either with respect to a particular aspects or examples (or one or more features thereof), or with respect to other Aspects (or one or more features thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described aspects or examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as aspects, examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An anchored dilator system comprising:
    a guide catheter having proximal and distal catheter end portions and a catheter lumen extending therebetween;
    an anchored dilator received in the catheter lumen, the anchored dilator includes:
        a dilator tip having an anchor cuff;
        a push tube coupled with the dilator tip and extending toward the proximal catheter end portion;
        a cuff operator proximate the dilator tip; and
        an operator shaft coupled with the cuff operator, the operator shaft extends from the dilator tip toward the proximal catheter end portion; and
    wherein the anchor cuff is configured to transition between anchored and shuttle configurations:
        in the anchored configuration actuation of the cuff operator with the operator shaft deploys the anchor cuff into engagement with the distal catheter end portion, and the anchor cuff has an anchored profile equal to or greater than a lumen profile of the guide catheter; and
        in the shuttle configuration the anchor cuff is withdrawn and disengaged with the distal catheter end portion, and the anchor cuff has a shuttle profile smaller than a lumen profile of the guide catheter.

2. The anchored dilator system of claim 1, wherein the dilator tip includes a dilator nose distal to the anchor cuff, the dilator nose tapers distally from the anchor cuff toward the push tube.

3. The anchored dilator system of claim 1, wherein the dilator includes a dilator transition proximate the anchor cuff, and in the anchored configuration the dilator transition is flush with an exterior surface of the guide catheter.

4. The anchored dilator system of claim 3, wherein in the shuttle configuration the anchor cuff includes a shuttle profile, and in the anchored configuration the anchor cuff includes an anchored profile larger than the shuttle profile.

5. The anchored dilator system of claim 1, wherein in the shuttle configuration the dilator tip is joined with the guide catheter to form a unitary composite device.

6. The anchored dilator system of claim 1, wherein the anchor cuff is a pliable anchor cuff, and the deployed anchor cuff in the anchored configuration includes an expanded anchor cuff.

7. The anchored dilator system of claim 1, wherein the cuff operator includes an operator bulb coupled with the operator shaft.

8. The anchored dilator system of claim 1, wherein the distal tip includes a cavity surface surrounding an operator cavity, and the cuff operator is received in the operator cavity.

9. The anchored dilator system of claim 8, wherein at least a portion of the anchor cuff is proximate the cuff operator and the cavity surface, and the cavity surface includes a tapered interface.

10. The anchored dilator system of claim 9, wherein in the anchored configuration the cuff operator is configured to engage the tapered interface and expandably deploy the tapered interface and the anchor cuff into engagement with an interior surface of the guide catheter.

11. An anchored dilator comprising:
a push tube having proximal and distal push tube portions;
a dilator tip coupled with the distal push tube portion, the dilator tip is configured for selectable coupling with a catheter, the dilator tip includes:
a cavity surface surrounding an operator cavity;
an anchor cuff having a cuff interface, the anchor cuff is configured to transition between a shuttle configuration having a shuttle profile and an anchored configuration having an anchored profile larger than the shuttle profile; and
a dilator nose distal to the anchor cuff; and
a cuff operator assembly configured to transition the anchor cuff between the anchored and shuttle configurations, the cuff operator assembly includes:
a cuff operator movably coupled with the dilator tip, and the cuff operator is received in the operator cavity;
an operator shaft coupled with the cuff operator, the operator shaft extends toward the proximal push tube portion; and
wherein actuation of the cuff operator with the operator shaft transitions the anchor cuff between the shuttle configuration and the anchored configuration.

12. The anchored dilator of claim 11, wherein the dilator nose tapers distally from the anchor cuff toward the push tube.

13. The anchored dilator of claim 11, wherein the dilator tip includes a dilator transition proximate the anchor cuff, in the shuttle configuration the dilator transition is proximate to the push tube, and in the anchored configuration the dilator transition is remote to the push tube relative to the shuttle configuration.

14. The anchored dilator of claim 11, wherein the anchor cuff is a pliable anchor cuff, and the anchor cuff in the anchored configuration includes an expanded anchor cuff.

15. The anchored dilator of claim 11, wherein the cuff operator includes an operator bulb coupled with the operator shaft.

16. The anchored dilator of claim 11, wherein the cavity surface includes a tapered interface, and in the anchored configuration the cuff operator is configured to deform the tapered interface and expand the anchor cuff to the anchored profile.

17. The anchored dilator of claim 11, wherein the cuff operator is in a distal position in the shuttle configuration, and in a proximal position in the anchored configuration.

18. The anchored dilator of claim 11, wherein the cuff operator is slidably coupled along the push tube.

19. The anchored dilator of claim 18, wherein the operator shaft is slidably coupled along the push tube.

20. The anchored dilator of claim 11 comprising a hub assembly proximate the proximal push tube portion, the hub assembly includes:
a dilator hub coupled with the proximal push tube portion; and
an operator hub coupled with a proximal shaft portion of the operator shaft.

21. The anchored dilator of claim 20, wherein the hub assembly includes an operator drive interposed between the dilator hub and the operator hub, and the operator drive is configured to actuate the operator shaft, move the cuff operator and transition the anchor cuff between the shuttle and anchored configurations.

22. The anchored dilator of claim 21, wherein the operator drive includes a threaded interface between the dilator hub and the operator hub.

23. A method for using an anchored dilator system comprising:
passing a dilator having a dilator tip coupled with a push tube through a catheter lumen of a catheter, an interior surface of the catheter surrounds the catheter lumen; and
anchoring the dilator tip with the catheter with an anchor cuff, anchoring the dilator tip includes:
passing a dilator nose of the dilator tip past a distal catheter portion of the catheter;
delivering the anchor cuff of the dilator tip toward the distal catheter portion through the catheter lumen, the anchor cuff in a shuttle configuration having a shuttle profile smaller than a lumen profile of the catheter;
transitioning the anchor cuff from the shuttle configuration to an anchored configuration, the anchor cuff in the anchored configuration having an anchored profile larger than the shuttle profile, and the anchored profile is equal to or larger than the lumen profile of the catheter; and
engaging the anchor cuff in the anchored configuration with the interior surface of the catheter.

24. The method of claim 23 comprising delivering the catheter and the dilator tip to a specified vascular location.

25. The method of claim 24, wherein delivering the catheter and the dilator tip includes:
manipulating the dilator tip with the push tube; and
guiding movement of the catheter with the dilator tip having the anchor cuff in the anchored configuration and engaged with the interior surface of the catheter.

26. The method of claim 23, wherein transitioning the anchor cuff from the shuttle configuration to the anchored configuration includes expanding the anchor cuff.

27. The method of claim 23, wherein the anchor cuff includes a pliable anchor cuff, and transitioning the anchor cuff from the shuttle configuration to the anchored configuration includes deforming the anchor cuff.

28. The method of claim 23, wherein the distal tip includes a cuff operator coupled with an operator shaft, and transitioning the anchor cuff from the shuttle configuration to the anchored configuration includes:
moving the cuff operator toward the anchor cuff with the operator shaft; and
biasing the anchor cuff into the anchored configuration with the cuff operator.

29. The method of claim 23, wherein engaging the anchor cuff with the interior surface of the catheter includes engaging the anchor cuff in surface to surface contact with the interior surface of the catheter proximate to the distal catheter portion.

30. The method of claim 23, wherein transitioning the anchor cuff from the shuttle configuration to the anchored configuration includes blending a dilator nose of the dilator tip with an exterior surface of the guide catheter.

* * * * *